United States Patent [19]

Cuscurida et al.

[11] 4,356,330

[45] Oct. 26, 1982

[54] METHOD OF DECOLORIZING MIXTURES OF T-BUTYL ALKYLPHENOLS WITH N-(2-HYDROXYETHYL)OXAZOLIDINE

[75] Inventors: Michael Cuscurida; George P. Speranza, both of Austin, Tex.

[73] Assignee: Texaco Inc., White Plains, N.Y.

[21] Appl. No.: 284,905

[22] Filed: Jul. 20, 1981

[51] Int. Cl.$^3$ .............................................. C07C 37/68
[52] U.S. Cl. ................... 568/756; 568/757; 568/749; 568/758; 568/759
[58] Field of Search ............... 568/756, 759, 758, 749, 568/957

[56] References Cited

U.S. PATENT DOCUMENTS

| | | | |
|---|---|---|---|
| 3,306,938 | 2/1967 | Welch et al. | 260/624 |
| 3,369,024 | 2/1968 | Masutugu | 260/2.2 |
| 3,375,284 | 3/1968 | Zika et al. | 260/613 |
| 3,437,699 | 4/1969 | Flickinger | 260/621 |
| 3,454,654 | 7/1969 | Hobbs | 260/623 |
| 3,546,302 | 12/1970 | Asadorian et al. | 260/619 |
| 3,660,317 | 2/1971 | Brannuck | 260/294.3 |
| 3,687,999 | 8/1972 | Kapur et al. | 260/458 |
| 3,723,529 | 3/1973 | Pitts | 260/583 N |

FOREIGN PATENT DOCUMENTS

| | | | |
|---|---|---|---|
| 1157236 | 11/1963 | Fed. Rep. of Germany | 568/749 |
| 1160860 | 1/1964 | Fed. Rep. of Germany | 568/784 |
| 1502518 | 11/1967 | France . | |
| 1597867 | 8/1970 | France . | |
| 46-2897 | 1/1971 | Japan . | |
| 46-6869 | 2/1971 | Japan . | |
| 49-31631 | 3/1974 | Japan . | |
| 52-68134 | 6/1977 | Japan . | |
| 6516378 | 6/1966 | Netherlands . | |
| 807736 | 1/1959 | United Kingdom | 568/756 |
| 807901 | 1/1959 | United Kingdom | 568/756 |
| 919428 | 2/1963 | United Kingdom | 568/756 |

OTHER PUBLICATIONS

Derwent Belgium Patent Report, vol. 88, May 11, 1962, p. 1 of sect. 5, #608268.
Abram, J. C., et al., "Mechanism of Color Removal by Ion Exchange Resins", Sucr. Belge/Sugar Ind. Abstr., vol. 90, No. 11, 1971, pp. 525–532.
Urban, M., et al., "Hydrazine Hydrate as Antioxidant Additive for Monohydric Phenols", Sb. Pr. Vyzk. Chem. Vyuziti Uhli, Dehtu Ropy, No. 10, 1970, pp. 65–78.

*Primary Examiner*—Werren B. Lone
*Attorney, Agent, or Firm*—Carl G. Ries; Jack H. Park; David L. Mossman

[57] ABSTRACT

A method of eliminating color-causing impurities in mixtures of t-butyl alkylphenols by treatment with N-(2-hydroxyethyl)oxazolidine at 90° C. and at atmospheric pressure is described. These phenols are used as peroxide inhibitors in polyoxyalkylene glycols for polyurethane foams. Discoloration of the polyol occurs if the phenol mixture is not treated with N-(2-hydroxyethyl)oxazolidine. The t-butyl alkylphenol mixture is derived from an alkylphenol made over an acid catalyst.

3 Claims, No Drawings

METHOD OF DECOLORIZING MIXTURES OF T-BUTYL ALKYLPHENOLS WITH N-(2-HYDROXYETHYL)OXAZOLIDINE

BACKGROUND OF THE INVENTION

1. Field of the Invention

The invention relates to methods for treating mixtures of alkyl substituted phenols so that they will not cause discoloration when used as peroxide inhibitors in polyols and more particularly relates to methods of treating mixtures of alkyl substituted phenols by means of the addition of N-(2-hydroxyethyl)oxazolidine.

2. Prior Art

Many decolorizing agents now in use remove color by physical adsorption. The most common materials to remove color by this means are represented by charcoals, blacks (such as carbon black), clays and earths. Other compounds remove color by chemical reaction and are frequently more specific as to the materials they can remove color from than the physical adsorption agents. While attempts have been made to predict compound colors, such as by electronegative or steric contributions of substituents to aromatic rings, numerous exceptions to rules relating color to structure require color prediction to be based largely on empirical observations.* As a result, attempts to remove color from a specific compound tend to be strictly trial and error operations.

*Griffiths, John. Colour and Constitution of Organic Molecules. London: Academic Press (1976), pp. 89–90.

Specific examples may be seen in the decolorization of amines. U.S. Pat. No. 3,723,529 describes the decolorization of polyethylene polyamines through the use of a heated activated carbon treatment. The decoloration of ethylene amines may also be accomplished by heating the ethylene amines with zinc, aluminum or tin, or a combination thereof together with sodium hydroxide and/or potassium hydroxide according to the method described in Japanese Kokai No. 69-2209.

Activated carbon is frequently used as a method for purifying drinking water. Water may also be decolorized and decontaminated by contact with ozone as noted by R. D. Gabovich, et al. in *Gig. Sanit.* Vol. 34, No. 6, 1969, pp. 18–22 (Chemical Abstracts citation 71:53407k).

Other materials are well known as decolorizers; for example, ion-exchange resins. J. C. Abram, et al., in *Sucr. Belge/Sugar Ind. Abstr.* Vol. 90, No. 11, 1971, pp. 525–32, describe color removal in substances such as polyethylene glycol and phenol by means of ion-exchange resins. U.S. Pat. No. 3,660,317 discloses that ion-exchange resin beads may be used to decolorize and deodorize materials and absorb ammonia. Ion-exchange resins may also be used to remove the metallic impurities from bis(2-hydroxyethyl) terephthalate by the method described in French Pat. No. 1,566,485. Tertiary-aminocyclobutanes that have electronegative substituents have been found to be useful color stabilizers and antioxidants in gasoline according to U.S. Pat. No. 3,369,024.

With regard to the instant invention, a problem arose in finding a substitute for 2,6-di-t-butyl-p-cresol which is used as a peroxide inhibitor in commercial polyol formulations. As the supplies of the p-cresol became short, other compounds were tried as inhibitors. It was found that di-t-butyl nonylphenol would give the desired peroxide inhibiting effect and would help prevent scorching of the resultant foam made from the polyol formulation. However, it was discovered that this inhibitor would cause undesirable discoloration of the polyol. It is therefore an object of this invention to find an agent which will remove the color from the nonylphenol-based inhibitor.

A number of methods have been devised for purifying phenols and substituted phenols. For example, U.S. Pat. No. 3,437,699 reveals that phenol may be purified of color-forming impurities by treatment with hydrogen in the presence of a hydrogenation catalyst such as nickel-molybdenum. Mixtures containing o-hydroxybenzoic acids and saturated aliphatic polybasic acids and/or polybasic phosphoric acids or phosphoric acid esters may be added to phenol to give a color-stable product according to French Pat. No. 1,502,518.

Mono- and dicarboxylic acids are effective to prevent the discoloration of phenols such as 2,6-diisopropylphenol according to Netherlands Appl. No. 6,516,378. Compounds somewhat similar to those decolorized by the instant invention are p-tert-butylphenol and nonylphenol which may be decolorized by the addition of small amounts of hydrazine or hydrazine hydrate as described in Japanese Kokai 77-68,134. Urban, et al. in *Sb. Pr. Vyzk. Chem. Vyuziti Uhli, Dehtu Ropy* No. 10, 1970, pp. 65–78 note that hydrazine hydrate improved the color stability of mixed monohydric phenols only in the absence of iron. The addition of powdered iron or an iron strip to alkylphenols such as 2,4-di-t-butylphenol and triisopropylphenol prevents coloration as French Pat. No. 1,597,867 discloses. Brominating phenols such as 4,4'-isopropylidenediphenol makes products of improved color and purity through the method of U.S. Pat. No. 3,546,302. Further, U.S. Pat. No. 3,454,654 discloses that 2,6-di-t-butyl-4-cresol may be used as a color stabilizer in the dibromination of phenol.

Color removal from substituted phenol polymers, such as poly(2,6-dimethyl-1,4-phenylene ether) may be effected by treating them with a reducing agent such as lithium aluminum hydride, sodium borohydride or sodium hydride as noted in Japanese Kokai No. 71-06,869. Addition of ammonium acetate and other such compounds can decolorize phenol-aromatic hydrocarbon-aldehyde resins as described in Japanese Kokai No. 71-02,897. Further, Japanese Kokai No. 74-31,631 discloses a method of producing p-alkylphenols without color by means of a distillation process. The decolorization of dialkylolalkylphenols, such as 2,6-dimethylol-4-nonylphenol, may be accomplished by adding dilute solutions of $H_2C_2O_4$ as shown in U.S. Pat. No. 3,306,938. Alkylphenol-ethylene oxide adducts and the sulfates thereof may be purified and decolorized by contacting the materials with an alkali metal borohydride as described in U.S. Pat. Nos. 3,375,284 and 3,687,999.

SUMMARY OF THE INVENTION

The invention is a method for removal of color-forming bodies from a mixture of alkyl substituted phenols comprising reacting the mixture with a portion of an N-(2-hydroxyalkyl)oxazolidine of the formula

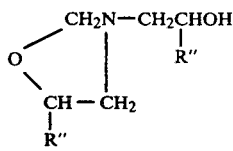

where R″ represents hydrogen or a lower alkyl radical.

DETAILED DESCRIPTION OF THE PREFERRED EMBODIMENTS OF THE INVENTION

The nonylphenol found to be useful as a precursor to a peroxide inhibitor in polyol formulations may be produced by using an anionic ion-exchange resin catalyst such as a sulfonic acid resin to react propylene trimer with phenol. The nonylphenol may then be reacted with a three-fold excess of isobutylene in the presence of an acid catalyst to obtain a mixture of butyl-substituted phenols. The composition of the mixture used in the examples presented herein is mostly di-t-butyl nonylphenol, with some mono-6-t-butyl nonylphenol and nonylphenol.

Di-t-butyl nonylphenol (DTBNP) is a good antioxidant for stabilization of urethane polyols serving both to prevent peroxide formation in them and raise their decomposition point. However, flexible polyols (2,000–4,000 molecular weight ethylene oxide and propylene oxide adducts of glycerine) which are stabilized with DTBNP develop an off-hue yellow color on exposure to light. This in effect makes them unacceptable as a commercial product since flexible polyols should typically have a Pt-Co color of less than 50.

It is suspected that the color of the di-t-butyl nonylphenol mixture is due to small amounts of compounds that have one substitution and one vacancy for the ortho positions on the phenyl ring adjacent to the hydroxyl group. Such a compound may be represented by the following structure

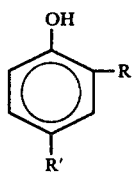

where R and R′ are the same or different alkyl groups. For the particular mixture of the examples herein, it is expected that the compound causing the color has R equal to a tert-butyl group and R′ equal to nonyl.

The decolorizing agents of this invention are N-(2-hydroxyalkyl)oxazolidines. These products are made by the reaction of formaldehyde with a dialkanolamine. It is theorized that this compound removes the color by reacting with the carbon in position 6 on the phenyl ring shown above. However, this proposed mechanism has not been confirmed at this point. The preferred oxazolidine is N-(2-hydroxyethyl) oxazolidine.

N-(2-hydroxyethyl)oxazolidine may be prepared as illustrated by the following equations $$(HOCH_2CH_2)_2NH + CH_2O \longrightarrow (HOCH_2CH_2)_2NCH_2OH$$

The N-(2-hydroxyethyl)oxazolidine used in the examples herein was prepared as follows:

Into a three-liter flask, fitted with a stirrer, a thermometer and a reflux condenser, were charged 150 g (5.0 moles) paraformaldehyde and 1575 g (15.0 moles) diethanolamine. The mixture was stirred until the formaldehyde had dissolved, at which time the temperature had risen to 50° C. Next, 300 g (10.6 moles) of paraformaldehyde was added incrementally over a thirty-minute period while the reaction temperature was kept at about 50° to 60° C. After a one-hour digestion period, water of condensation (235 g) was removed with aspirator vacuum to a pot temperature of 80° C. For purposes of the instant invention, the product could be used as is or it could be fractionally distilled at 90° to 95° C. at 5.0 mm Hg vacuum.

It has been found that treatment of a crude DTBNP product with about 1 to 5 wt.% of N-(2-hydroxyethyl)oxazolidine is effective in removing (or changing) the color forming bodies. Typically the treatment yields flexible polyols which have a Pt-Co color of less than 50 and which have a minimum tendency to discolor on exposure to light. The treatment involves mixing the N-(2-hydroxyethyl)oxazolidine with the crude DTBNP and heating the mixture for a time to encourage the reaction of the N-(2-hydroxyethyl)oxazolidine with the color-causing impurities. It is preferred that the temperature for the decolorization reaction be in the range of 25° to 150° C. and it is especially preferred that the temperature be about 90° C., but an optimum temperature for each kind of alkylphenol that could be treated in this way can be easily determined by experimentation. It could also be expected that other hydroxyethyl oxazolidines would have the effect of decolorizing the t-butyl alkylphenol mixtures. However, as explained earlier, discovering a chemical additive to remove color is largely a matter of trial and error. The color-removing additives tend to be specific to certain colored compounds or family of compounds.

The method of this invention is illustrated by the following examples.

EXAMPLE I

Use of DTBNP as a Polyol Costabilizer

This example will illustrate the preparation and use of DTBNP as a costabilizer for a 3,000 molecular weight ethylene oxide/propylene oxide adduct of glycerine (THANOL ® F-3016) which is a product of Texaco Chemical Co. It will further show the effectiveness of an antioxidant combination of 4,000 ppm DTBNP and 600 ppm octylated diphenylamine (VANLUBE ® 81, R. T. Vanderbilt Co.) in preventing peroxide formation and raising the decomposition point as measured by differential scanning colorimetry (DSC) of the resultant polyol. It will further show that THANOL F-3016, prepared using DTBNP, was off-hue in color initially and rapidly increased in color intensity on exposure to light. The DTBNP used in this experiment was prepared by reacting of 1100 g nonylphenol with 1135 g isobutylene using 11 g methane sulfonic acid for catalysis. The reaction was carried out in a tubular reactor (68 ml) at 130° C. using a flow rate of 50 ml/hr. The crude product was neutralized and stripped of unreacted volatiles prior to use. It contained greater than 90% DTBNP basis gas liquid chromatography analysis.

Into a ten-gallon kettle were charged 10 pounds of a 268.5 hydroxyl number ethylene oxide/propylene oxide adduct of glycerine which had an alkalinity of 25.5 mg KOH/g. The reactor was then evacuated and purged with prepurified nitrogen. A mixture of 37.4 pounds of propylene oxide and 1.4 pounds of ethylene oxide was then reacted at 105°–110° C. at 50 psig over a 5 hour period. Propylene oxide (1.5 pounds) was then reacted at 105°–110° C. The reaction mixture was then digested two hours to an equilibrium pressure. The alkaline product was then neutralized with 600 g of 25% aqueous oxalic acid. Di-t-butyl nonylphenol (91.3 g), octylated diphenylamine (13.5 g) and Hyflo Supercel filter aid (150 g) were also added at this time. The neutralized product was then vacuum stripped to a minimum pressure, nitrogen stripped and filtered at 105° C. The finished product had the following properties:

| | |
|---|---|
| Acid number, mg KOH/g | 0.025 |
| Hydroxyl number, mg KOH/g | 56.6 |
| Water, wt. % | 0.01 |
| Unsaturation, meq/g | 0.03 |
| pH in 10:6 isopropanol/water | 5.9 |
| Sodium, ppm | 0.2 |
| Potassium, ppm | 2.8 |
| Peroxide, ppm | 1.1 |
| Color, Pt—Co (initial) | ~50 (off-hue) |
| Color, Pt—Co (40 days in glass) | ~125 (off-hue green) |
| Decomposition point, °C. | 198 |

EXAMPLE II

First Treatment of DTBNP with N-(2-hydroxyethyl)oxazolidine

Into a 500 ml three-necked flask equipped with a stirrer, thermometer and nitrogen source were charged 100 g DTBNP and 1.0 g N-(2-hydroxyethyl)oxazolidine. The reactants were then heated at 88°–90° C. for three hours. The resultant product was a light brown low viscosity liquid. It was used without further purification in Example III.

EXAMPLE III

This example will illustrate the use of the N-(2-hydroxyethyl)oxazolidine-treated DTBNP in the stabilization of a 3,000 molecular weight propylene oxide/ethylene oxide triol prepared as in Example I. It will further show the improved color of the resultant product on storage whether the DTBNP is used alone or in combination with other inhibitors such as octylated diphenylamine or phenothiazine. The higher the Pt-Co number, the higher is the color intensity.

| Sample Number | Antioxidant, ppm | | Polyol Decomposition Point, °C. | Color, Pt—Co (Days Storage) | |
|---|---|---|---|---|---|
| 1 | DTBNP | (2,000) | 185 | 25–30 | (1) |
| | | | | 15–20 | (60) |
| 2 | DTBNP | (4,000) | 193 | 30–40 | (1) |
| | | | | 20 | (60) |
| 3 | DTBNP | (2,000) | 190 | 25 | (1) |
| | octylated diphenylamine | (200) | | 20 | (60) |
| 4 | DTBNP | (4,000) | 203 | 25–30 | (1) |
| | octylated diphenylamine | (600) | | 25–30 | (60) |
| 5 | DTBNP | (2,000) | 203 | 25–30 | (1) |
| | phenothiazine | (200) | | 25–30 | (60) |

We claim:
1. A method for removal of color-forming bodies from a mixture of t-butyl nonylphenols derived by reacting isobutylene with nonylphenol comprising reacting the mixture with N-(2-hydroxyethyl) oxazolidine in proportions of 1 to 5 weight percent of the mixture at a temperature in the range of 25° to 150° C.
2. The method of claim 1 in which the mixture to be reacted with N-(2-hydroxyethyl)oxazolidine contains 6-t-butyl nonylphenol.
3. The method of claim 1 or 2 in which the reaction temperature is about 88° to 90° C.

* * * * *